(12) United States Patent
Benja-Athon

(10) Patent No.: US 6,302,902 B1
(45) Date of Patent: Oct. 16, 2001

(54) DOUBLE-BLADDER PARAFFIN BAG

(76) Inventor: Anuthep Benja-Athon, 210 E. 30th St. Ground Floor, NY, NY (US) 10016

( * ) Notice: Subject to any disclaimer, the term of this patent is extended or adjusted under 35 U.S.C. 154(b) by 0 days.

(21) Appl. No.: 09/294,062

(22) Filed: Apr. 19, 1999

(51) Int. Cl.$^7$ .................................................. A61F 7/00
(52) U.S. Cl. ......................................... 607/104; 607/108
(58) Field of Search ..................... 607/96, 104, 108–112, 607/114

(56) References Cited

U.S. PATENT DOCUMENTS

| | | | | |
|---|---|---|---|---|
| 4,964,402 | * | 10/1990 | Grim et al. .......................... | 128/999 |
| 5,257,429 | * | 11/1993 | Genis ........................................ | 5/636 |
| 5,584,086 | * | 12/1996 | Van Winkle et al. ................. | 607/114 |
| 5,630,961 | * | 5/1997 | Salee ..................................... | 219/759 |
| 5,730,721 | * | 3/1998 | Hyatt et al. .............................. | 604/49 |

* cited by examiner

*Primary Examiner*—Linda C. M. Dvorak
*Assistant Examiner*—R. Kearney

(57) ABSTRACT

A portable double-bladder bag to transfer heat down a thermal gradient from heated fluid thereunto interfacing paraffin thereunto bodily structures of a human or an animal comprises a first bladder member comprises a heat-insulating flexible sheet member, a port with a reversibly closing lid on the sheet member and a second bladder member comprises a first inner sheet member within the cavity of the first bladder member and a second outer sheet member which is a physical continuity of the sheet member of the first bladder thence define the double-bladder bag. The port admits the heated fluid into the cavity of the first bladder member and a lid to reversibly close the opening of the port to contain the fluid within the cavity of the first bladder member. The second bladder has a closed cavity to contain and sequester paraffin and comprises of the aforementioned inner and outer sheet members adaptable to optimally conduct and radiate heat from the heated fluid to bodily structures of a human and animal in the application of thermal therapeutics without causing thermal injury. Two thermometric strips to detect, measure and visually display the incremental thermal gradient changes as a panel of distinctively different colors and degree numbers are permanently embedded within the substance of the paraffin.

10 Claims, 2 Drawing Sheets

DOUBLE-BLADDER PARAFFIN BAG

FIELD OF THE INVENTION

A compact double-bladder paraffin bag for heat application to human bodily structure without thermal injury.

BACKGROUND OF THE INVENTION

The first objective of the present invention is provide a readily available and inexpensive apparatus for effective and efficient means of application of heat therapeutics for the treatment of pain and inflammation of bodily structures of a human or an animal.

The second objective of the present invention is provide a safer, effective and efficient means of application of heat therapeutics for the treatment of pain and inflammation of bodily structures of a human or an animal.

The application of local thermotherapy by human is an ancient science. Thermal therapeutics produces desirable therapeutic effects on the local and distant structures such as the increase of extensibility of collagen tissues, decrease joint stiffness, pain relief, muscle spasm and stiffness relief, increase blood flow and enhance the removal of local waste metabolites and resolution of inflammatory infiltrates, edema and exudates. However, to data, thermotherapy is not only cumbersome to apply and not readily available but also can be hazardous in the application using the prior art which are in the market.

The use and application of heated paraffin which is an effective means of therapeutic heating of tissues suffer the above set backs so that a form of very inexpensive heat therapeutic modality is being withheld from most people such as people who suffer from all forms of arthropathy such as degenerative, rheumatoid, posttraumatic arthritis, etc., scleroderma and tissue and joint contracture who need and can benefit most.

There are several reasons for the above setbacks. First, the applicator of heated paraffin is cumbersome and is mostly set up and available in the health care providers' office and not readily available at homes of or in any settings where it is needed most and on a frequently and daily as-needed basis. Second, operation and maintenance of the paraffin bath are relatively expensive, need constant attention to keep the paraffin at molten state which consume electricity albeit small. Third, paraffin is messy and accidental spillage is common. Fourth, paraffin is flammable when exposed to a flame. Fifth, the application of molten paraffin on the body part require knowledge of application and use and the apparatus for said application is not available.

Molten paraffin is an excellent heat modality as paraffin has a low heat-carrying capacity and a poor thermal conductor as compare with water which has a high specific heat and thermal conductivity so that the application of molten paraffin is therapeutics while heated water at the same temperature can cause thermal injury to the tissues of the patient. Further discussion of paraffin heat can be had in the Therapeutic Heat and Cold, 4th ed., J. L. Lehmann (ed), Williams & Wilkins 1990. The molten paraffin should have a temperature range of 51.7° C. to 54.4° C. (F. H. Krusen: Physical Medicine. W. B. Saunders, Phila., 1942. G. K. Stillwell General principles of thermotherapy. In Therapeutic Heat and Cold. 2nd ed., S. Licht (ed), Waverly Press, Baltimore, 1965 pages 232–239).

The present invention solves the above setbacks and, for the first time, provides a compact, portable, easy-to-use-and-apply, safe and nonmessy means of application of paraffin as an effective heat modality for home and any settings for anyone including people with debilitating hands.

SUMMARY OF THE INVENTION

The use and application of molten paraffin for therapeutic heating of tissues in human and animal are cumbersome, complicated, mostly inaccessible and accidental spillage is common and messy. Worse, paraffin and the petroleum-based oils are flammable when exposed to a flame.

To overcome the aforementioned setbacks, the present invention provides a portable double-bladder bas to transfer heat down a thermal gradient from heated fluid such as, but not limited to, heated water, thereunto interfacing paraffin thereunto bodily structures of a human or an animal comprises a first bladder member comprises a heat-insulating flexible sheet member whereon a port with reversibly closing lid and a second bladder member comprises a first inner sheet member within the cavity of the first bladder and a second outer sheet member which also is a physical continuity of said flexible sheet member of said first bladder member. Therefore, said three sheet members define the double-bladder bag. The port admits the heated fluid into the cavity of the first bladder member and said lid reversibly closes the opening of the port to contain the fluid within the cavity of said first bladder member. Said second bladder member has a closed cavity to contain and sequester paraffin within said inner and outer sheet members both of which adaptable to efficiently conduct and radiate heat from the heated fluid to said paraffin to said bodily structures in the process of application of thermal therapeutics without causing thermal injury to said structures. Two thermometric strips detect, measure and visually display the incremental thermal gradient changes by a panel of distinctively different colors and numbers indicating degree Fahrenheit and/or Centigrade are permanently embedded within the substance of the paraffin. Both strips can be visualized through said three sheet members, fluid and paraffin.

DESCRIPTION OF THE PREFERRED EMBODIMENTS

Figure 1:
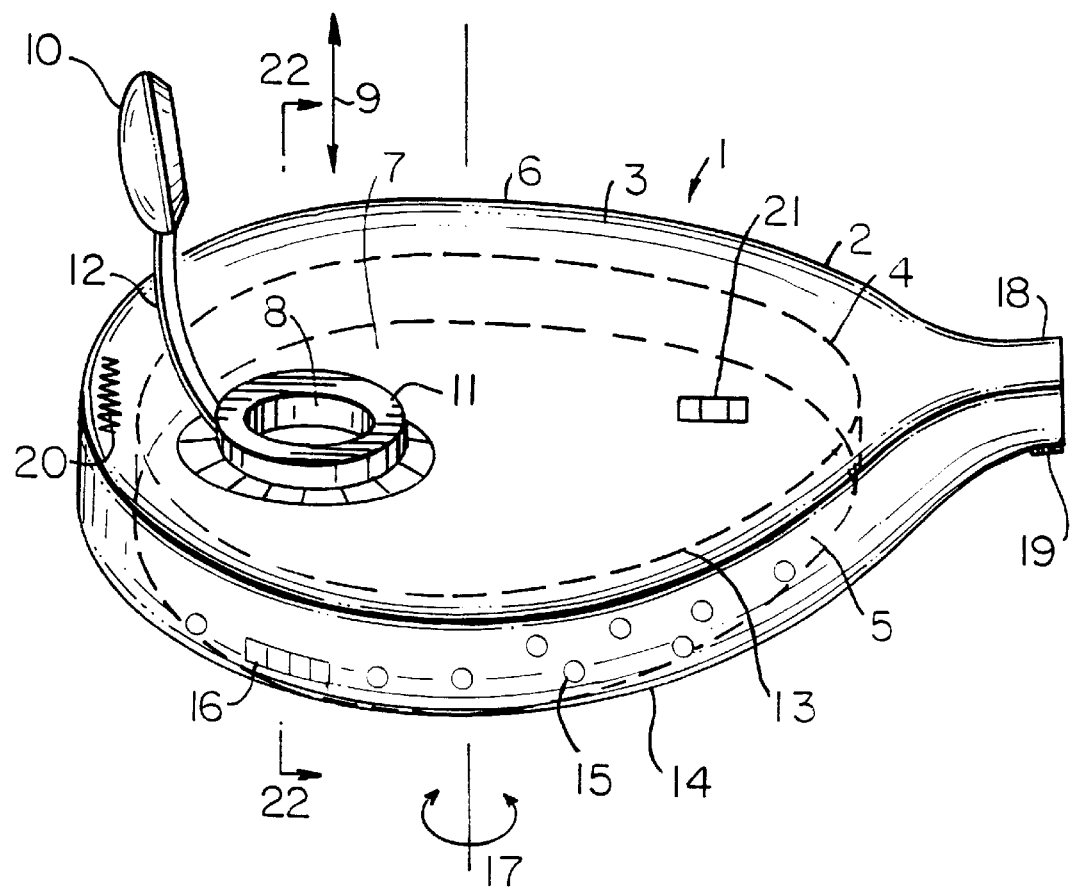
FIG. 1 is a schematic view of the present invention.

FIG. 1 shows the portable double-bladder bag 1 of the present invention. Bag 1 comprises a first outer bladder 2 forming a cavity 3 and a second inner bladder 4 within first outer bladder 2. Second inner bladder 4 forms a closed cavity 5. Bag 1 and, correspondingly, bladders 2 and 4, can have different configurations such as, but not limited, to oblong, rectangular, square or circular so that bag 1 can be effectively applied to and retained at any and all bodily parts such as hand, knee, ankle of the body of a person or an animal. First, bag 1 comprises a heat-insulating flexible sheet member 6 which defines cavity 3. Located on sheet member 6 is a circular port 7 with an opening 8 which admits heated fluid means such as heated tap water from a faucet into cavity 3 and also reversibly allows the jettison of said fluid means out of cavity 3 of bladder 2 as represent by single double arrow 9. A lid means 10 of reversibly closing said opening of port 7 is attached to the rim of 11 by attachment 12 is used in the process of sequestering said fluid means within cavity 3. Said port-lid complex can be made from many standard port with reversible closure which is readily available commercially. Moreover, said port-lid complex can be made to be ergonomic so that patients with painful, inflamed hands with acute or chronic joint deformity can use bag 1 and said port-lid complex with ease. In addition, one of the advantageous features of bag 1 is that bag 1 can be independently rested in the sink or bathtub and said port with the lid on the side can be positioned just under and aligned with the faucet of said sink or bathtub so that heated water flows into cavity 3 through port 7 without the hands of the user of bag 1 being in the thermal harm way. Lid 10 can then be applied on port 7 to create a reversibly-closed cavity 3 containing said heated water which can be reversibly expelled from cavity 3 by decanting cooler water as shown by as represent by single double arrow 9.

Second inner bladder 4 comprises a first inner sheet member 13 and a second outer sheet member 14 thence forming closed cavity 5 wherein contained and sequestered paraffin and petroleum-based oils 15. The petroleum-based oils affect the melting point or the temperature of solid-to-liquid transition phase of paraffin and solid-liquid state of solid and liquid paraffin. First inner sheet member 13 is in contact with cavity 3 and with said heated fluid when cavity 3 is filled with said heated fluid. Second outer sheet member 14 is exposed to air and bodily structures (not shown in the figure) during the use of bag 1 in thermal therapeutics. Moreover, second outer sheet member 14 is physical continuity of heat-insulating flexible sheet member 6 thence sheet member 14 and sheet member 6 defines cavity 3 wherein first inner sheet member 13 is in contact with said fluid means. However, the materials used to manufacture sheet member 6 and outer sheet member 14 may be of different thickness and/or composition for the reasons explained and described in this preferred embodiments.

Heat-insulating flexible sheet member 6 is manufactured from heat-insulating material such as rubberized materials including latex, neoprene, polyvinyl chloride (PVC) plastic including transparently clear PVC, flocked PVC, nylon, modern microfabric materials and any combination thereof which confer sheet member 6 with the physical property of poor heat conduction and radiation so that bag 1 can be physically handled by the person using said bag when bag 1 contains heated fluid. Furthermore, said physical property promotes the unilateral heat transfer down the thermal gradient from said heated fluid to the paraffin to the bodily structures as in the claims. In all instances, the use of said manufacturing materials in the production of a transport sheet member 6 is desirable to allow the user of bag 1 to easily view the thermometric device 16 during the application of the bag and the thermal therapeutics to obtain the optimal range of temperatures of the paraffin for heat treatment without inadvertent thermal injury to the bodily part or parts being treatment. The thickness of sheet member 6 is about 1 millimeter if it is made from PVC although other thicknesses can be used to confer sheet member 6 the insulating property and durability to withstand stress to prevent puncturing and rupture of bag 1.

Second inner bladder 4 is enclosed by cavity 3 and comprises first inner [wall] sheet member 13 whose material is made durable but yet very thin (a fraction of a millimeter) but durable film of heat-conducting and radiating material such as rubberized materials including latex, neoprene, polyvinyl chloride (PVC) plastic including transparently clear PVC, flocked PVC, nylon, metallic alloy, synthetic modern microfabric sheet and any combination thereof to optimize the conduction and radiation of said heat from said heated fluid to paraffin 15. Similarly, the second outer sheet member 14 is made durable but yet very thin (a fraction of a millimeter) sheet of heat-conducting and radiating material such as rubberized materials including latex, neoprene, polyvinyl chloride (PVC) plastic including transparently clear PVC, flocked PVC, nylon, metallic alloy, synthetic modern microfabric sheet and any combination thereof to optimize the conduction and radiation of said heat from paraffin 15 to said bodily part or parts without the escape of the paraffin molecules from closed cavity 5 of second inner bladder 4. In other words, said materials making sheet members 13 and 14 impermeable to paraffin 15 thus prevent the leakage of paraffin 15 from closed cavity 5 into cavity 3 and/or into open space. Paraffin 15 is installed into second inner bladder 4 during manufacturing process of bag 1. In all instances, the use of said manufacturing materials in the production of transparent inner sheet member 13 and outer sheet member 14 is desirable to allow the user of bag 1 to easily view of thermometric device during the application of the bag and the thermal therapeutics to obtain the optimal range of temperatures of the paraffin for heat treatment without inadvertent thermal injury to the bodily part or parts being treatment.

Bag 1 can be used in any circumstances and setting such as kitchen or bathroom where there is a source and supply of heated fluids of which heated water from a faucet is most readily available and fulfill said objectives. Therefore, on a thermal gradient, the present invention utilizes the heated tap water which is readily available in all modern home and institution to provide sufficient and safe form of heat transform, i.e. melt, paraffin 15 from a solid to liquid state. The heat in molten paraffin in turn transfers said heat to the tissues of a person or an animal (not shown in figure) which are placed in contact with outer sheet member 14. Since bag 1 including first outer bladder 2 and second inner bladder 4 are made from flexible material, bag 1 can be folded, for example, about an axis as represents by curved double arrow 17 so that bag 1 can wrapped around said bodily structure and retained in wrap position using the tongue 18 provided as an extension of flexible sheet member 6 created during manufacturing process. Tongue 18 is either a direct extension of the materials used to make flexible sheet member 6 or attached to sheet member 6 during manufacturing process. On tongue 18 and flexible sheet member 6 is hooks 19 and loops 20 means (VELCRO) which engage to complete a loop around said bodily structures for effectively applied to and retained bag 1 at any and all bodily parts such as hand, knee, ankle of the body of a person or an animal.

Thermometric device comprises of two thermometric strips 16 and 21 which are permanently embedded within paraffin substance 15 and fixed to outer sheet member 14 and within closed cavity 5 of second inner bladder 4 during manufacturing process. Thermometric strips 16 and 21 detect, measure and visually display the incremental thermal gradient changes within paraffin 15 during said heat transfer. The commercially available thermometer which display a panel of distinctively different colors and/or degree Fahrenheit or Centigrade with temperature changes is used. The advantage of said positioning of strips 16 and 21 is that strips 16 and 21 are closest to said bodily structures to be heated so that the strips 16 and 21 detect, measure and visually display the most accurate temperature closest to said bodily structures. In addition, when bag 1 is folded and used an discussed supra, strips 16 and 21 are used to monitor the temperature on both sides of said bodily structures.

Visualization of strips 16 and 21 is only possible if transparent features of sheet members 6, 13 and 14 is used. Alternatively, not shown in the figure, numerous independent thermometric devices which are commercially available thermometers capable of displaying a panel of distinctively different colors and/or degree Fahrenheit of Centigrade with temperature changes can be used. Said devices can be used to monitor and visually display the temperature changes of said heated fluid and paraffin 15 with the thermometric monitoring probes in direct contact with sheet members 6 and 14 and electrical leads connect said probes to said independent thermometric devices.

Figure 2:
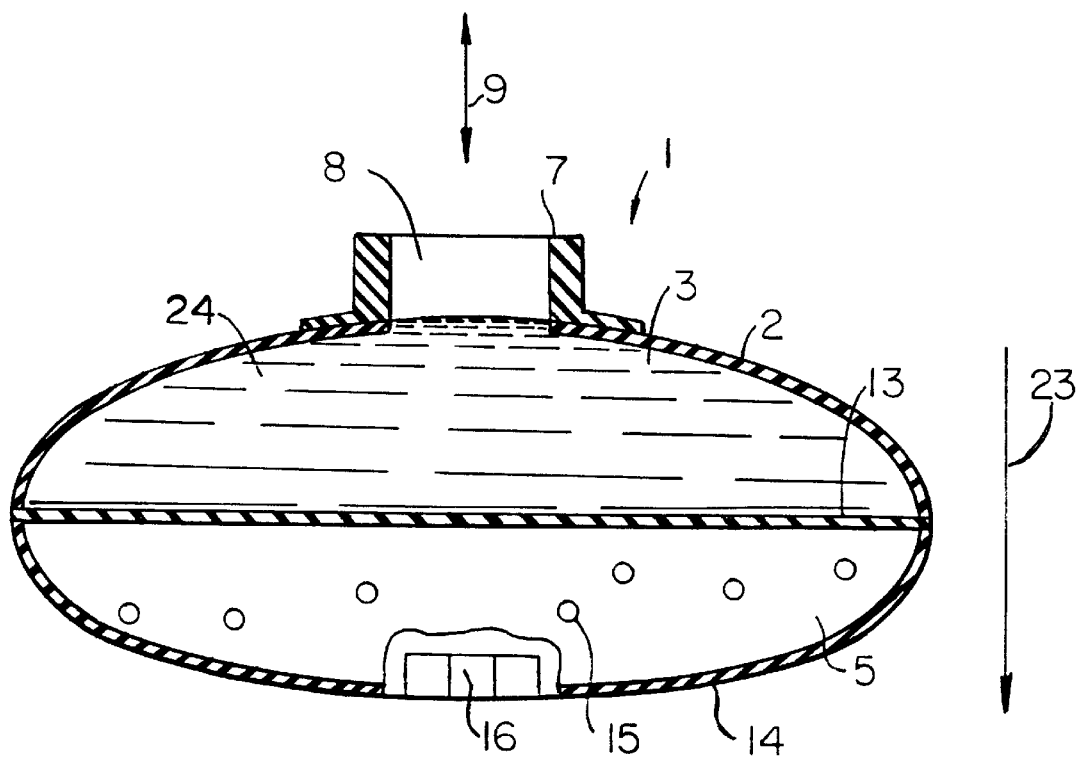
FIG. 2 is a schematic view of the present invention at section 22 in FIG. 1.

FIG. 2 shows the portable double-bladder bag 1 of the present invention at cross-section 22 in FIG. 1. As discussed supra, on a thermal gradient as represent by straight single arrow 23 for the heat transferred is from heated tap water 24 which was admitted into cavity 3 to paraffin 15 to the bodily structures of a person or an animal (not shown in figure) which are placed in contact with outer sheet member 14. After the therapeutic heat treatment of said structures, like warm water 24 can be discussed by reversibly expelled from cavity 3 through opening 8 of port 7. Then bag 1 can be stored away to await reuse.

Although various preferred embodiments of this invention have been described, it will be appreciated by those skilled in the art that variations may be made without departing from the spirit of the invention or the scope of the aforementioned claims.

What is claimed is:

1. A portable double-bladder bag for transferring heat down a thermal gradient comprising:

a first bladder member means for containing and sequestering a heated fluid;

a second bladder means for containing paraffin;

wherein said second bladder means is located within said first bladder means;

a port coupled to said first bladder means; and a thermoplastic means within said second bladder for measuring and visually displaying thermal gradient changes within said paraffin during said heat transfer.

2. The portable double-bladder bag according to claim 1 wherein said first bladder is inflatable and comprises a flexible sheet member structured to form a cavity.

3. The portable double-bladder bag according to claim 1 wherein said second bladder means for containing paraffin comprises an inner flexible sheet member and an outer flexible sheet member.

4. The portable double-bladder bag according to claim 1 wherein said first bladder member means comprises a flexible sheet member which is a physical continuity of an outer flexible sheet member of said second bladder.

5. The portable double-bladder bag according to claim 4 wherein said outer flexible sheet member of said second bladder and together with said flexible sheet member of said first bladder forms a cavity of said second bladder.

6. The portable double-bladder bag according to claim 1 wherein said port has an opening for the admission of said fluid into and emission of said fluid out of said first bladder.

7. The portable double-bladder bag according to claim 6 wherein said port further comprises a lid means for reversibly closing said port in the process of sequestering said fluid within said first bladder.

8. The portable double-bladder bag according to claim 1 wherein said thermometric means comprises two thermometric strip means for detecting, measuring and visually displaying incremental temperature changes of the paraffin and visually indicating and displaying said thermometric changes by a panel of distinctively different colors.

9. The portable double-bladder bag according to claim 8 wherein said thermometric strips are permanently embedded within said paraffin.

10. The portable double-bladder bag according to claim 8 wherein said thermoplastic strips are permanently fixed to the outer sheet member of said second bladder.

* * * * *